(12) United States Patent
Kuru et al.

(10) Patent No.: US 12,296,074 B2
(45) Date of Patent: May 13, 2025

(54) COLLECTION PANELS FOR BATHROOM AEROSOLS

(71) Applicant: Kohler Co., Kohler, WI (US)

(72) Inventors: William Kuru, Plymouth, WI (US); Clayton Garrels, Kohler, WI (US); William Kalk, Sheboygan, WI (US)

(73) Assignee: Kohler Co., Kohler, WI (US)

( * ) Notice: Subject to any disclaimer, the term of this patent is extended or adjusted under 35 U.S.C. 154(b) by 350 days.

(21) Appl. No.: 17/697,634

(22) Filed: Mar. 17, 2022

(65) Prior Publication Data

US 2022/0313864 A1 Oct. 6, 2022

Related U.S. Application Data

(60) Provisional application No. 63/169,685, filed on Apr. 1, 2021.

(51) Int. Cl.
| | | |
|---|---|---|
| *B01D 53/02* | (2006.01) | |
| *A61L 9/20* | (2006.01) | |
| *B03C 3/00* | (2006.01) | |
| *B03C 3/47* | (2006.01) | |
| *F21V 33/00* | (2006.01) | |

(52) U.S. Cl.
CPC ........ *A61L 9/20* (2013.01); *B03C 3/00* (2013.01); *B03C 3/47* (2013.01); *F21V 33/0088* (2013.01); *A61L 2209/111* (2013.01); *A61L 2209/12* (2013.01)

(58) Field of Classification Search
CPC ........... A61L 2209/111; A61L 2209/12; A61L 2209/22; A61L 9/01; A61L 9/16; A61L 9/20; A61L 9/205; B03C 3/00; B03C 3/016; B03C 3/28; B03C 3/30; B03C 3/41; B03C 3/47; B03C 3/60; B03C 3/86; F21V 33/0088
See application file for complete search history.

(56) References Cited

U.S. PATENT DOCUMENTS 5,741,352 A * 4/1998 Ford ................. B03C 3/155
96/99
5,802,623 A * 9/1998 Vincent .............. E03D 9/052
4/209 R
(Continued)

FOREIGN PATENT DOCUMENTS

CN 201271392 Y 7/2009
CN 206074302 U 4/2017
(Continued)

OTHER PUBLICATIONS

Examination Report from Indian Application No. 202214019231, dated Nov. 22, 2022, 6 pages.
(Continued)

*Primary Examiner* — Christopher P Jones
(74) *Attorney, Agent, or Firm* — Lempia Summerfield Katz LLC (57) ABSTRACT

A panel for accumulation of aerosol particles in an indoor environment includes a surface plate and an electrostatic collector plate coupled to the surface plate and configured to hold an electrical charge to attract and accumulate aerosol particles. The panel may include or otherwise be coupled with an activation device.

16 Claims, 9 Drawing Sheets

(56) References Cited

U.S. PATENT DOCUMENTS

| | | | |
|---|---|---|---|
| 5,938,823 A * | 8/1999 | Condit | B03C 3/017 |
| | | | 96/225 |
| 8,241,398 B2 | 8/2012 | Berry et al. | |
| 8,409,335 B2 | 4/2013 | Dyson et al. | |
| 9,381,459 B2 | 7/2016 | Stark et al. | |
| 2005/0186871 A1* | 8/2005 | Hockaday | A61L 2/232 |
| | | | 442/76 |
| 2006/0104858 A1* | 5/2006 | Potember | A61L 9/205 |
| | | | 422/123 |
| 2009/0010801 A1 | 1/2009 | Murphy et al. | |
| 2009/0041632 A1* | 2/2009 | Day | A61L 9/205 |
| | | | 422/121 |
| 2010/0047115 A1 | 2/2010 | Krichtafovitch et al. | |
| 2011/0162526 A1 | 7/2011 | Tatsumi et al. | |
| 2016/0243559 A1 | 8/2016 | Kim et al. | |
| 2018/0214586 A1* | 8/2018 | Louis | H01J 37/32348 |
| 2018/0258693 A1 | 9/2018 | Hall et al. | |
| 2019/0090056 A1 | 3/2019 | Rexach et al. | |
| 2022/0112704 A1* | 4/2022 | Garrels | A61L 2/22 |
| 2023/0416690 A1* | 12/2023 | Kuno | C12M 23/04 |

FOREIGN PATENT DOCUMENTS

| | | |
|---|---|---|
| CN | 111358996 A | 7/2020 |
| JP | H08309148 A | 11/1996 |

OTHER PUBLICATIONS

Extended European Search Report from European Patent Application No. 22163666.5, dated Dec. 1, 2022, 15 pages.

Extended European Search Report from European Patent Application No. 22163666.5, dated Mar. 3, 2025, 12 pages.

Chinese Office Action from Chinese Patent Application No. 202210336456.X, dated Feb. 20, 2025, 11 pages. (including English summary).

* cited by examiner

COLLECTION PANELS FOR BATHROOM AEROSOLS

CROSS REFERENCE TO PRIOR APPLICATION

This application claims priority benefit of Provisional Application No. 63/169,685 filed Apr. 1, 2021, the content of which is hereby incorporated by reference in its entirety.

FIELD

The present application relates generally to aerosol collection in indoor environments.

BACKGROUND

Aerosols may be removed from the air that humans breathe by the human body's respiratory system. However, some aerosols may be toxic or even carry a virus into the human body. The problem of aerosols may be mitigated through sanitization of the air. Airborne aerosols in commercial and residential bathrooms often contain bacteria and pathogens that are harmful to humans if they are inhaled. These aerosols result from toilet flushing, faucets running, hand dryers, urinals, and drain splashes. Without proper ventilation or collection, aerosols can accumulate in bathrooms—especially in high use situations. Harmful biology within the aerosol droplets may be a risk to human infections for many hours if it remains airborne and is not removed or captured.

BRIEF DESCRIPTION OF THE DRAWINGS

Exemplary embodiments are described herein with reference to the following drawings, according to an exemplary embodiment.

DETAILED DESCRIPTION

The following embodiments are directed to the problem of aerosol accumulation in bathrooms or other areas by collecting the aerosols from the environment. Aerosols may be introduced into the environment from the flush of a toilet (e.g., plume), open drains, humans, lavatory usage, air drying, or other ways. Along with the aerosols, any microbiology contained within them such as viruses are also collected. The devices in these embodiments reduce the aerosol concentration within the bathroom and consequently increases the health and hygiene of the bathroom environment.

Natural sinks such as venting, ductwork, and fans provide effective solutions to reducing aerosol concentrations in bathrooms, but placement of these ventilation devices is often chosen by convenience or other non-empirical knowledge. Incorrect placement could inadvertently cause aerosols to spread undesirably throughout the bathroom. Locations where these ventilation devices are installed are often in convenient proximity to 'behind-the-wall' resources, or where they 'fit' between adjacent rooms. The design of the airflow within the bathroom is not prioritized if considered at all. Consequently, the accumulation and persistence of aerosols in bathrooms can vary considerably. Some commercial bathrooms may include no venting at all. In nearly all scenarios, there are more sources for the aerosols than sinks for the aerosols.

The following embodiments increase the collection rate of the riskiest bathroom aerosols in the regions where they are most often created—near the plumbing fixture where they are in highest concentration. It may be desirable to collect the aerosols before the ventilation system spreads the aerosols throughout the bathroom or potentially to other rooms in the vicinity. As an example, an electrostatic collection device may be placed behind the toilet or urinal. Other heated surfaces may be placed in proximity to surfaces such as mirrors. The electrostatic collection device may be integrated with light fixtures, coat hangers, toilet paper hangers, towel racks or other devices in the bathroom.

The advantage of these devices is collection devices that they collect the aerosol particles passively at the source. These collection devices also collect the aerosol particles continuously, thus providing a steady technique for removing particles from the air in the bathroom. Overall, these devices would help to clean the air in the bathroom and create a heathier and more hygienic environment.

Figure 1:
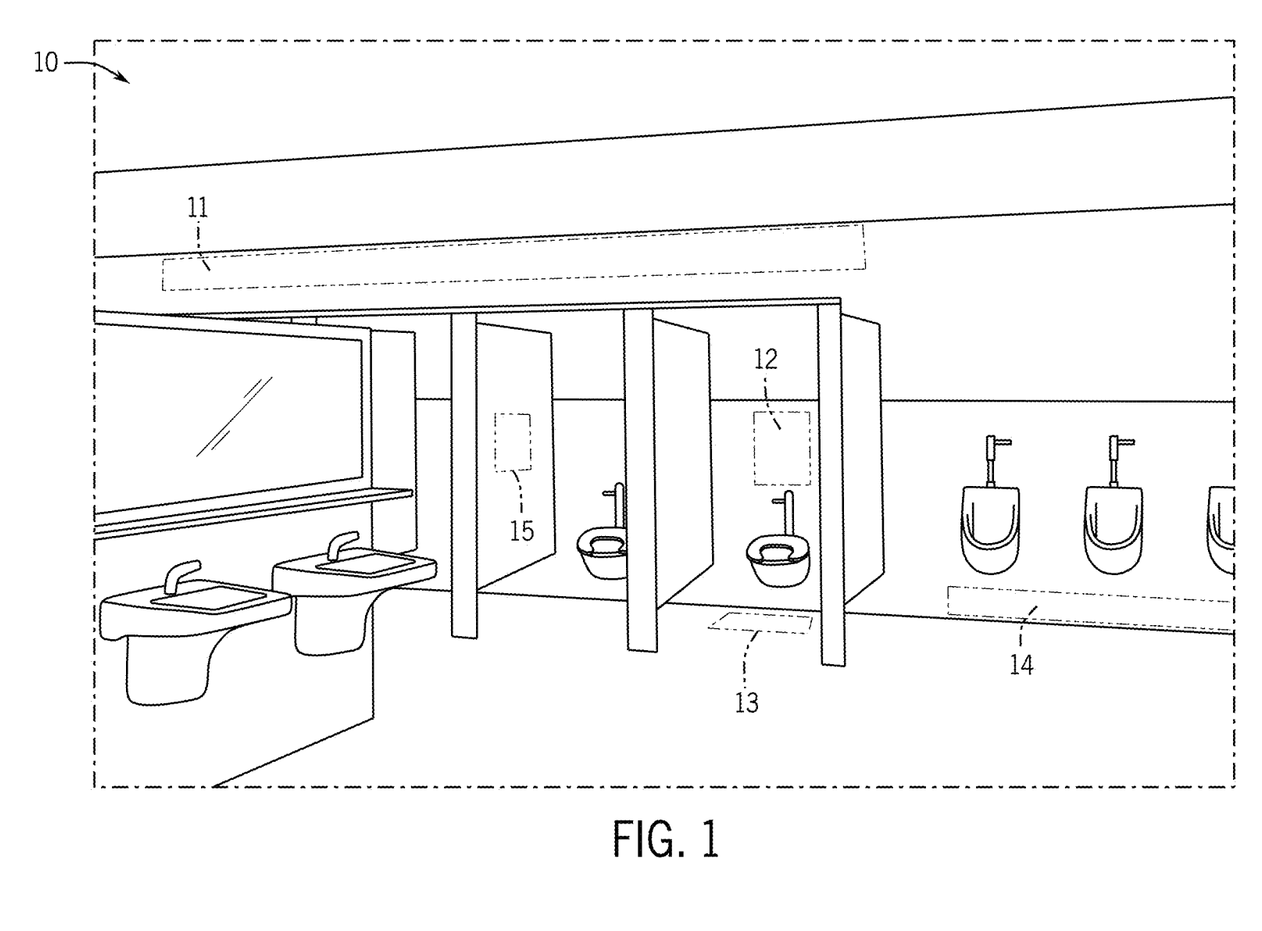
FIG. 1 illustrates an example bathroom setting for various embodiments of an electrostatic aerosol collector.

FIG. 1 illustrates an example bathroom setting for various embodiments of an electrostatic aerosol collector configured to attract and retain aerosol particles from the air. Other types of particles may be collected and retained. The electrostatic aerosol collector could be integrated into various bathroom fixtures without being overt. The electrostatic aerosol collector could be integrated into a toilet, for example, it may be coupled to the side, front or back of a toilet tank or toilet pedestal. Similarly, the electrostatic aerosol collector could be coupled to a urinal or span across multiple urinals. The electrostatic aerosol collector could be coupled to the wall of a bathroom stall or another divider. For example, the divider may be installed between urinals or between lavatories.

FIG. 1 illustrates a bathroom setting 10 where the electrostatic aerosol collector is placed in various locations. Additional, different, or fewer locations may be used.

An example electrostatic aerosol collector 11 is suspended from the ceiling or integrated in the ceiling. One or more mounts (e.g., brackets, arms, or extensions) may mount the electrostatic aerosol collector 11 to a ceiling joist or another support associated with the ceiling. The electrostatic aerosol collector 11 may be at a predetermined height from the floor (e.g., 7 feet or 2 meters) that is out of reach of the typical user. The electrostatic aerosol collector 11 may be suspended at a predetermined distance from the ceiling (e.g., 2 feet or 1 meter) so that sufficient airflow is maintained between the electrostatic aerosol collector 11 and the ceiling. The electrostatic aerosol collector 11 may be integrated with or coupled to a ventilation system (e.g., vent and/or duct).

The electrostatic aerosol collector 11 may be used in place of a ceiling tile. That is, a ceiling tile may be removed and an electrostatic aerosol collector 11 having a similar size as the ceiling tile may be installed in its place. The electrostatic aerosol collector 11 may include any of the activating devices and supported apparatus as described in any embodiment herein.

Multiple units of the electrostatic aerosol collector 11 may be installed in a predetermined pattern on the ceiling. Examples patterns may include staggered or checkerboard patterns. Each unit of the multiple units may be spaced at least a predetermined distance from other units. The electrostatic aerosol collectors 11 may be arranged in rows along a length of the room. The electrostatic aerosol collectors 11 may be angled in different directions.

An example electrostatic aerosol collector 12 is placed by the toilet. The electrostatic aerosol collector 12 may include any of the activating devices and supported apparatus as described in any embodiment herein. The electrostatic aerosol collector 12 may be mounted on the wall behind the toilet.

The electrostatic aerosol collector 12 may be integrated with the toilet. The electrostatic aerosol collector 12 may be directly connected or otherwise coupled to a tank of the toilet. The electrostatic aerosol collector 12 may be directly connected or otherwise coupled to a flush valve of the toilet (e.g., wall-mounted toilet). The electrostatic aerosol collector 12 may be positioned between a water supply pipe and the wall.

An example electrostatic aerosol collector 13 is placed on the floor. The electrostatic aerosol collector 13 may include any of the activating devices and supported apparatus as described in any embodiment herein. The electrostatic aerosol collector 13 on the floor may be placed in a space where users will not stand. Example placement may be under a wall-mounted toilet. The floor mounted electrostatic aerosol collector 13 may be deactivated by the presence of a user. For example, the electrostatic aerosol collector 13 is only active when a user's presence is not detected. Example sensors include weight sensors, proximity sensors, and motion sensors. The presence of the user triggers the electrostatic aerosol collector 12 to turn off and it is turned back on after a predetermined time period.

An example electrostatic aerosol collector 14 spans the space behind multiple urinals. The electrostatic aerosol collector 14 may include any of the activating devices and supported apparatus as described in any embodiment herein. The electrostatic aerosol collector 14 may be wall-mounted and span more than twice the width of a urinal.

An example electrostatic aerosol collector 15 may be integrated with a divider that divides space between adjacent urinals, adjacent toilets, adjacent lavatories, or other adjacent bathroom devices. The divider is a partial wall that is mounted to the floor, ceiling, and/or wall. The electrostatic aerosol collector may be integrated with or otherwise coupled to the divider.

In some embodiments, the electrostatic aerosol collector is biased with a voltage to provide the electrostatic charge. The voltage may be a low voltage that avoids the risk of shock. In some embodiments, the electrostatic aerosol collector is charged through the physical properties of the material. In some embodiments, the electrostatic aerosol collector is charged through frictionally moving two components together. In order to maintain the electrostatic charge on the plastic sheet, the sides, edges, or corners may be insulated. The insulation may include non-conductive materials between the plastic sheet and the wall or other devices.

As the electrostatic aerosol collector builds up particles, which may include organic particles as well as inorganic particles such as dust, the electrostatic aerosol collector may be cleaned by a user or cleaned automatically. The user may wipe the electrostatic aerosol collector in order to clean it.

The surface area of the electrostatic aerosol collector may be related to the number of aerosols that are collected. Larger surfaces may collect more particles at a higher rate. Thus, the electrostatic aerosol collector may be implemented in many locations or in large locations such as along a wall, behind a mirror, or on dividers between stalls. Air movement with the room may improve transfer of aerosol particles to the collection surface.

Figure 2:
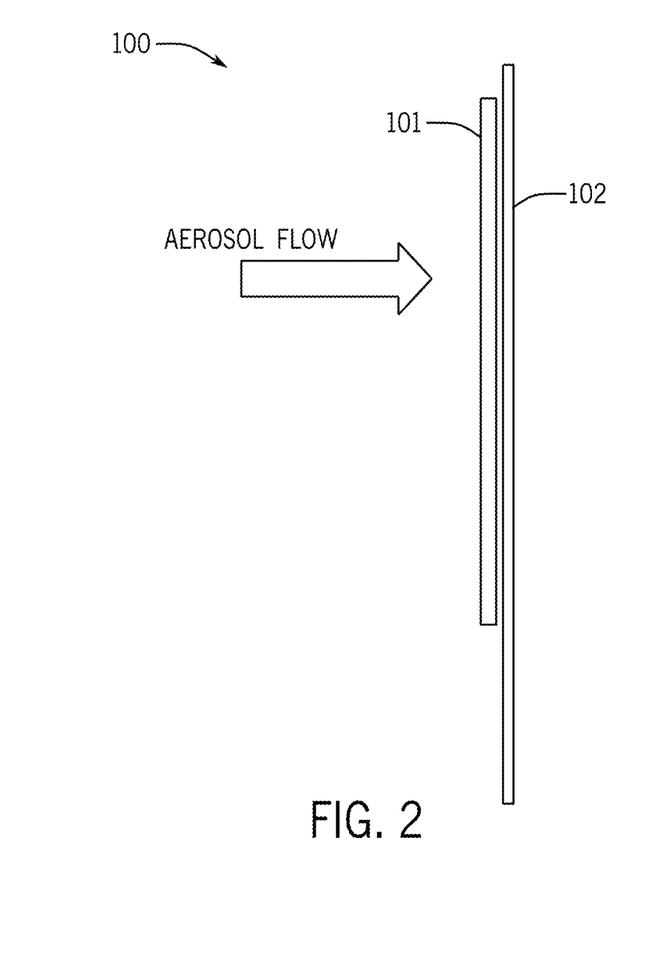
FIG. 2 illustrates a first embodiment for the electrostatic aerosol collector.

FIG. 2 illustrates a first embodiment of a system 100 for the electrostatic aerosol collector 101 that is mounted on a wall 102. The example of FIG. 2 may be implemented in any of the locations shown in FIG. 1. In this example, the electrostatic aerosol collector 101 is formed from a plastic sheet. The plastic sheet may retain a charge from manufacturing. For example, in an injection mold for plastics, molecules may become aligned and impart a charge on the surface. Additionally, the plastics may obtain their charge due to the triboelectric effect. This is caused when materials are rubbed together and separated during production. Material handling may create the triboelectric effect. As a result, in this example, no external charge is imparted on the electrostatic aerosol collector 101 but the plastic sheet still attracts aerosols.

Alternatively, the electrostatic aerosol collector 101 may be connected to a charger or another type of charging element. The charging element provides the electrical charge to the electrostatic collector plate 101. The charging element may be connected to the electrostatic aerosol collector 101 by a wire or another conductive element. The charger may be turned on or off in response to commands from a controller. The charger may be turned on or off responsive to detection of a user.

Figure 3:
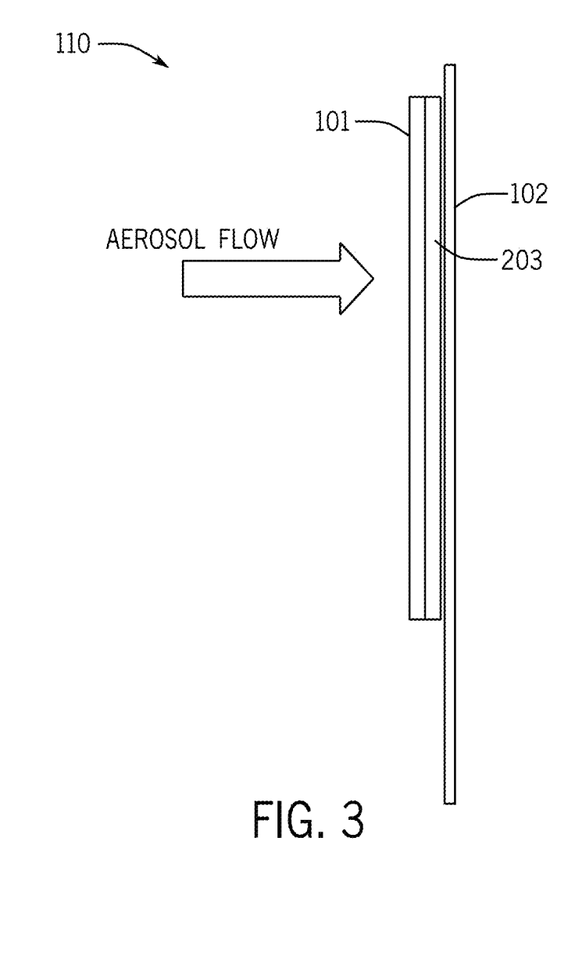
FIG. 3 illustrates a second embodiment for the electrostatic aerosol collector.

FIG. 3 illustrates a second embodiment system 110 for an electrostatic aerosol collector 101 mounted on a wall 102. The example of FIG. 3 may be implemented in any of the locations shown in FIG. 1. In this embodiment, two dissimilar metals are placed in adjacent positions or otherwise in proximity to each other. One metal has an affinity for electrons than the other metal. The affinity may be measured as the change in energy of a neutral atom when an electron is added. The dissimilar metals may be separated by a dielectric material.

In some examples, the electrostatic aerosol collector 101 with two dissimilar metals generates an electrostatic charge under specific environment conditions. One condition may be the relative humidity. The electrostatic aerosol collector 101 may generate a substantial electrostatic charge when the relative humidity is in excess of 50% or another RH level. The charge may be different polarities according to the acid-base characteristic of the surfaces of the metals.

The two dissimilar metals may include any two metals with a predetermined difference (e.g., relatively large difference) In the respective anodic index sufficient for the metals to develop a potential. Example pairs of the two dissimilar metals may include copper and iron, zinc and iron, nickel and aluminum, nickel and lead, and copper and aluminum.

In some examples, both the dissimilar metals may be exposed to the air. That is, the dissimilar metals may be positioned adjacently rather than stacked. Each of the metals may be charged with a different polarity. That is, one of the metals may hold a positive charge and one of the metals may hold a negative charge. A first type of aerosol particles may be attracted to the positive charge. A second type of aerosol particles may be attached to the negative charge.

Figure 4:
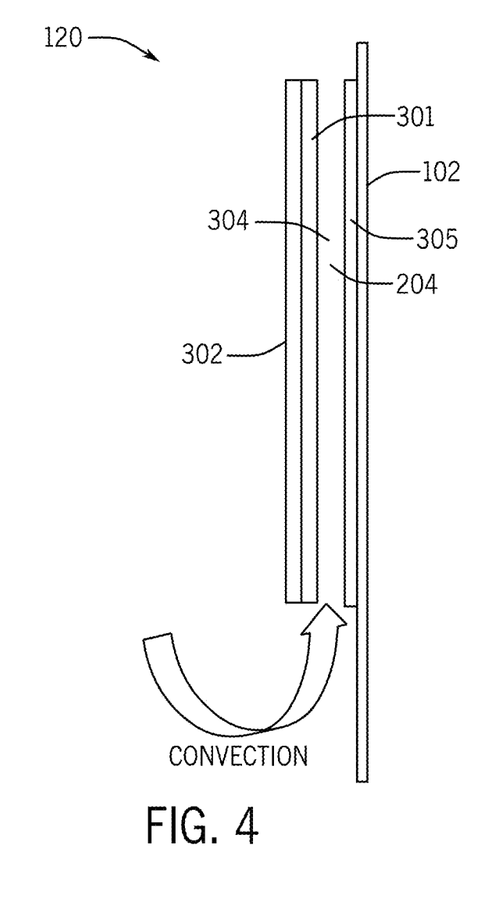
FIG. 4 illustrates a third embodiment for the electrostatic aerosol collector.

FIG. 4 illustrates a third embodiment system 120 for the electrostatic aerosol collector plate 301 couple to a surface substrate 302 (e.g., surface plate or show surface). The example of FIG. 4 may be implemented in any of the locations shown in FIG. 1. The surface substrate 302 may include a mirror or a sign. A medicine cabinet may be configured to include the electrostatic aerosol collector plate 301 behind the cabinet or behind the door.

In the example of a mirror, the surface substrate 302 may include a glass substrate that is polished and applied with a metallic coating such as aluminum. In the case of a sign, the substrate 302 may include various types of plastics, ceramics, or polymers.

The collection surface of the electrostatic aerosol collector plate 301 may be opposite of the surface substrate 302. The electrostatic collector plate 301 is coupled to the surface plate and configured to hold an electrical charge to attract and accumulate aerosol particles. The electrostatic aerosol collector plate 301 may be spaced apart from the wall 102 so that a space 304 separates the electrostatic aerosol collector plate 301 from the wall 102. As air circulates through the space 304, aerosol particles are attracted to the electrostatic aerosol collector plate 301.

The mirror may be a plastic or glass substrate having a coating to cause the reflection. The reflective surface of the mirror layer may be a two-way mirror so that a display is visible through the mirror. The display may include a light emitting diode (LED) or liquid crystal display (LCD). Images from the display appear overlaid on the reflection from the mirror.

In addition, as an alternative to the aerosol collector plate 301, the glass substrate of the mirror may have an activatable coating such as titanium oxide ($TiO_2$). The activatable coating may be activated by UV light or 405 nanometer light. The activatable coating may include a catalyst that is stimulated in the presence of water vapor to generate a reactive species of oxygen (e.g., hydrogen peroxide, ozone, hydroxyl, superoxide, hydroperoxyl, or others).

In addition, the third embodiment system 120 may include a heating element 305. The heating element 305 may heat the air in the space 304, causing convection or air flow from the heated air the rises out of the space 304. The heating element 305 may be spaced apart from the electrostatic collector plate by a predetermined distance. The heating element may also prevent the mirrored surface from fogging.

The electrostatic aerosol collector plate 301 and the surface substrate 302 may be retractable for cleaning. In other words, the system 120 may include a hinge or other pivoting assembly for swinging the electrostatic aerosol collector plate 301 and the surface substrate 302 out and away from the space 304 and the heating element 305. In this retracted position, a user can easily wipe the surface of the aerosol collector plate 301 or perform another cleaning technique.

Figure 5:
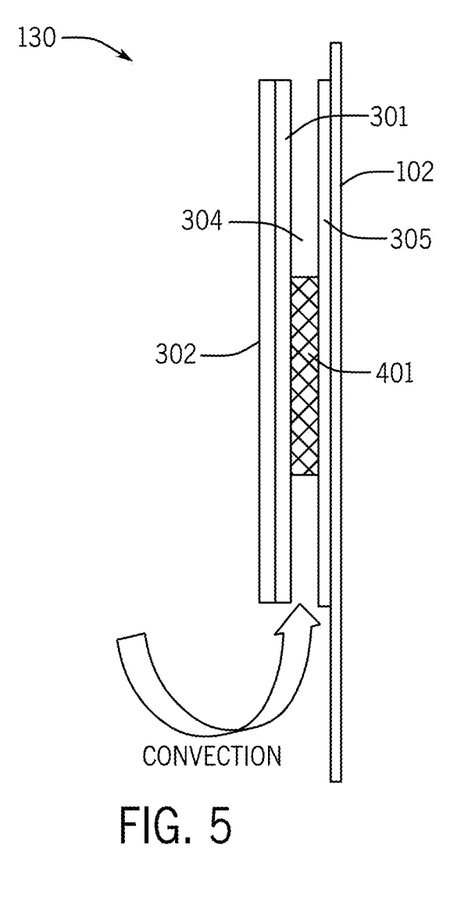
FIG. 5 illustrates a fourth embodiment for the electrostatic aerosol collector.

FIG. 5 illustrates a fourth embodiment system 130 for the electrostatic aerosol collector 301. The example of FIG. 5 may be implemented in any of the locations shown in FIG. 1. In this example, a treatment device 401 may be included in the space 304.

The treatment device 401 may include a light source, such as an ultraviolet light source. The light source may provide light for the light fixture. The light source may be configured to cause convection to move air including the aerosol particles past the electrostatic collector plate.

The light source may have a wavelength of approximately 405 nanometers, for example, 400-410 nanometers. The light source may eliminate or otherwise have antimicrobial affects against bacteria, bacterial biofilms, endospores, yeasts, fungi, and viruses.

The treatment device 401 may include a fin, vent, or other structure that has a coating. The fin may extent perpendicular into the space 304 from the electrostatic aerosol collector 301 or at another angle. The coating may include titanium dioxide configured to disinfect the collected aerosols. The coating may be applied directly to the electrostatic aerosol collector 301. The coating may be another material having a disinfectant property.

The coating, such as titanium dioxide, may be a photocatalyst. The combination of the light source and the photocatalyst may be capable of breaking down organic materials such as bacteria, bacterial biofilms, endospores, yeasts, fungi, and viruses.

The treatment device 401, for example including the fin or vent, may be easily removed by the user for cleaning. The treatment device 401 may be washed in a sink or a machine (e.g., dishwasher). The treatment device 401 may be wiped clean by the user or technician.

A fan may be included in space 304. The fan may provide air circulation through the space 304. The air circulation increases the number of aerosol particles retained by the electrostatic aerosol collector 301.

As discussed in more detail below, any combination of the fan, the heating element, and/or the electrostatic collector plate may be powered by a power source. If power is desired, a DC voltage is applied between the plates, or between a plate and a corona wire. The airborne particles are charged and attracted to the plate of opposite charge. Various control techniques may be applied automatically by a controller or manually by user input.

Figure 6:
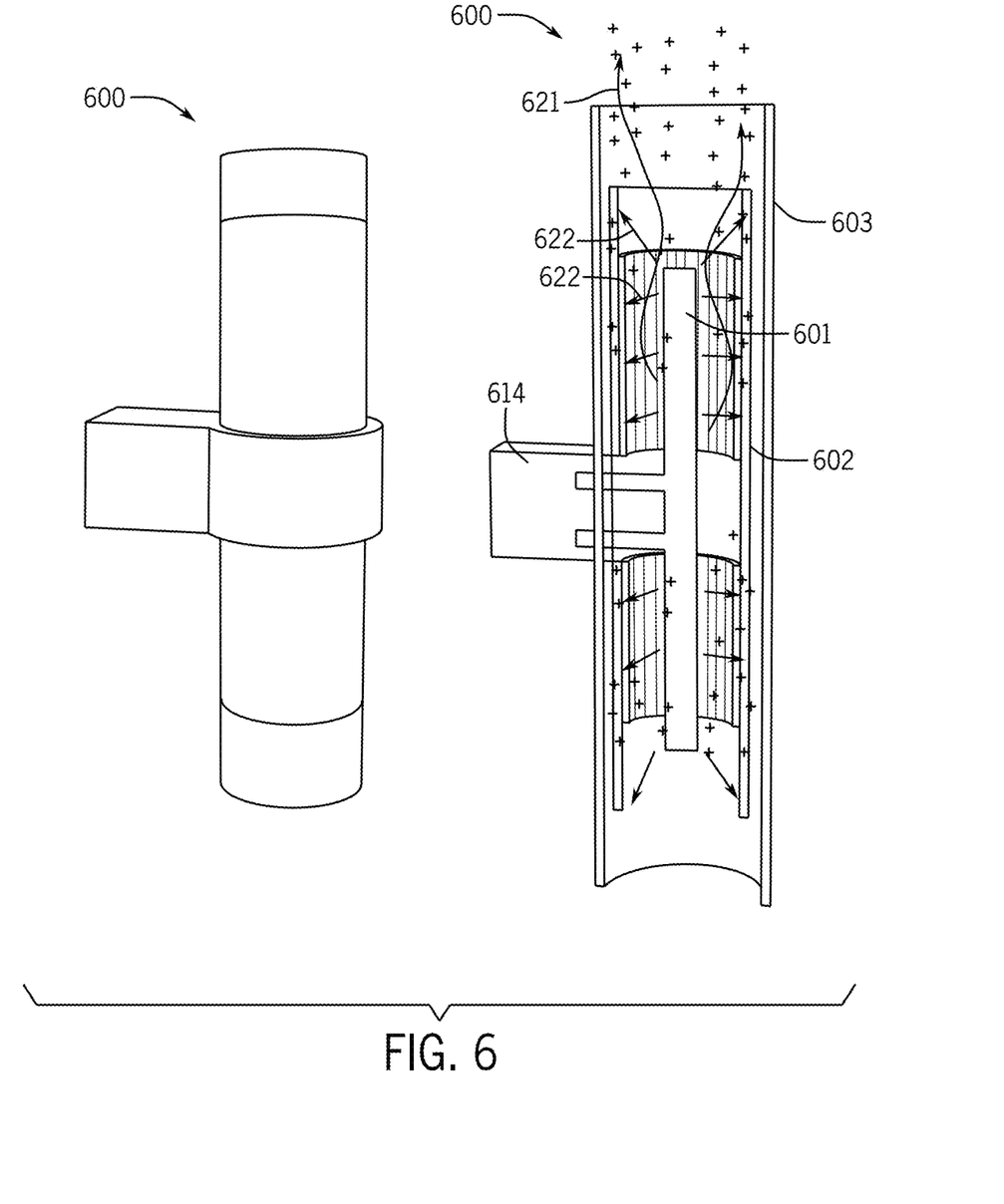
FIG. 6 illustrates a light sconce using any of the first four embodiments.

FIG. 6 illustrates an example light sconce 600 for implementing the electrostatic aerosol collector. For example, a light 601 (e.g., 405 nm light) may be provided in the sconce 600 adjacent to a collector plate 602. In addition, or as an alternative to the light, a heating element may be provided in the sconce 600. Heated air within the sconce 600 causes cooler air to flow in from the bottom of the sconce 600 and out through the top of the sconce 600. The charged collector plate 602 will attract and retain aerosol particles as they pass through the sconce.

The sconce 600 may include an outer housing 603 that surrounds the light 601 and the collector plate 602. The sconce 600 may be mounted or otherwise coupled to a wall, ceiling, or other surface using support 614. The support may include one or more fasteners (e.g., screw, bolt, hook) and a bracket or plate for the fasteners to secure the sconce 600 to a mounting position.

The air flow through the sconce 600 may be generally in one direction such as the longitudinal direction of the sconce 600, as shown by arrow 621. The flow of air may be aided by a fan or follow natural circulation of the room. In addition, or in the alternative, the light 601 may generate heat (as shown by arrow 622), which cause convection for the flow of air through the sconce 600.

Figure 7:
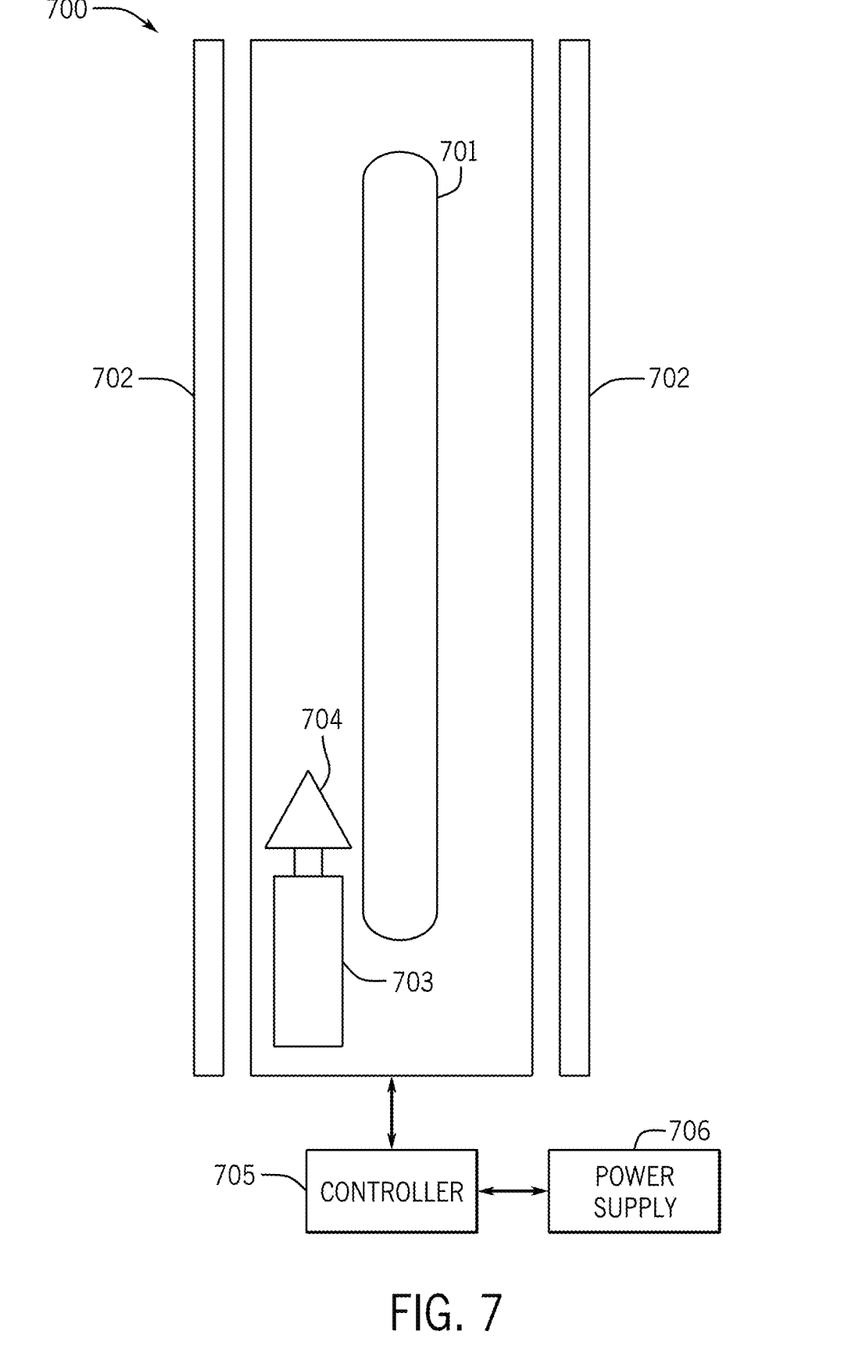
FIG. 7 illustrates another embodiment light sconce.

FIG. 7 illustrates another example light sconce 700. The light sconce 700 includes an interior light 701 and a collector plate 702. The interior light 701 and/or the collector plate 702 may be partially enclosed or substantially enclosed by a housing. The housing may surround the interior light 701 and the collector plate 702. The housing may be between the interior light 701 and the collector plate 702. The interior light may include a light source (e.g. 400-410 nanometers or ultraviolet) to eliminate or otherwise have antimicrobial affects against particles at or near the collector plate 702. An exterior light may also be included outside of the housing.

The light sconce 700 may also include a misting device 704 connected to a reservoir 703. The misting device 704 is configured to generate a mist or spray. Liquid, such as water or hydrogen peroxide, is drawn from the reservoir 703 and converted to small droplets that are sprayed into the air inside the sconce 700. The mist increases the humidity and increases the reactivity of the light on the aerosol particles. The misting device 704 may include a piezoelectric element.

The sconce 700 may also be attached to a controller 705 and/or power supply 706. The controller 705 is configured to generate commands for operations of the sconce 700. Light commands may turn the exterior light on and off. Charger commands may turn a bias on the collector plate 702 or set the level of the charge. UV commands may turn on or off the interior light 701 or set the duration, wavelength, or intensity of the interior light 701. In some examples, the interior light 701 is only turned on when the exterior light is turned off, and vice versa. In some examples, the interior light 701, such as the 405 nanometer light, may cast a blue or near blue hue. The blue hue may not be preferable for some users. Some users may prefer to turn the interior light 701 off when the user is physically present. Other users may prefer to leave the interior light 701 on at all times to maximize the sanitization effect.

A sensor may detect the ambient environment and provide data to the controller 705 such that any of the commands are based on the collected sensor data. For example, a light sensor or motion sensor may detect when the room is vacant. In response to this sensor data, the controller 705 may generate a UV command and/or a charger command. Another example sensor may detect aerosols in the vicinity of the sconce 700. The controller 705 may generate a UV command and/or a charger command in response to a certain type of aerosol or a predetermined concentration of aerosols.

Figure 8:
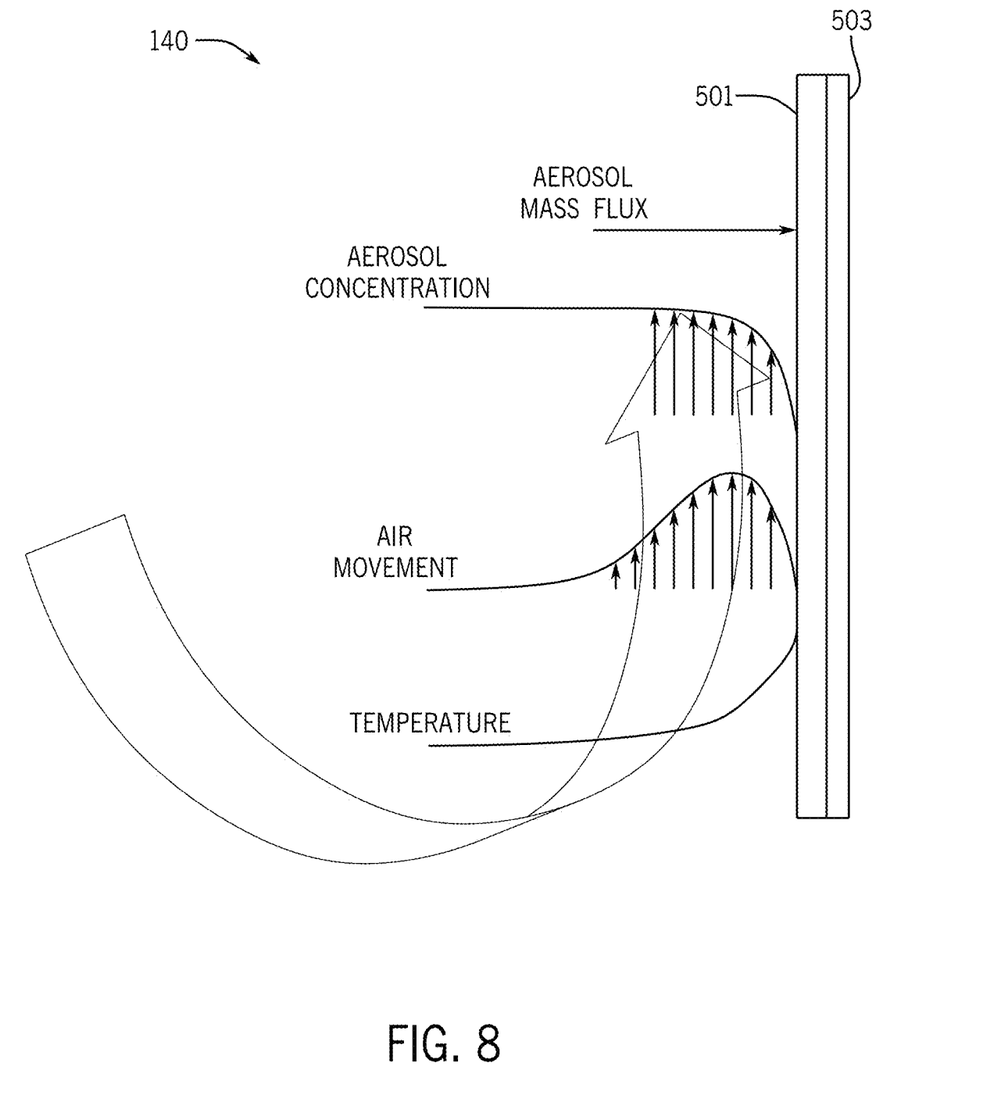
FIG. 8 illustrates an example mass transfer surface.

FIG. 8 illustrates an example mass transfer surface in a collection system 100 in a fifth embodiment. In this embodiment, a heating element 503 is paired with a surface plate 501. The surface plate 501 is configured to accumulate aerosol particles. The heating element 503 is configured to increase the mass transfer of the aerosol particles on the surface plate. The heated surface creates a buoyancy effect near the $TiO_2$ coated mirrored surface to reduce the thickness of the stagnant boundary layer that forms. The buoyancy of the air also enhances the aerosol mass transfer to the treated surface. Once aerosols contact the surface they react and are treated. Overall, there is a mass flux of aerosols to the mirrored surface. As the contact time for the particles on the surface plate 501 is increased, there is an improvement in the availability to scrub the particles. For example, the ability of the light source and the photocatalyst to break down organic materials is improved. The effectiveness may increase further by using taller mirrored surfaces.

Figure 9:
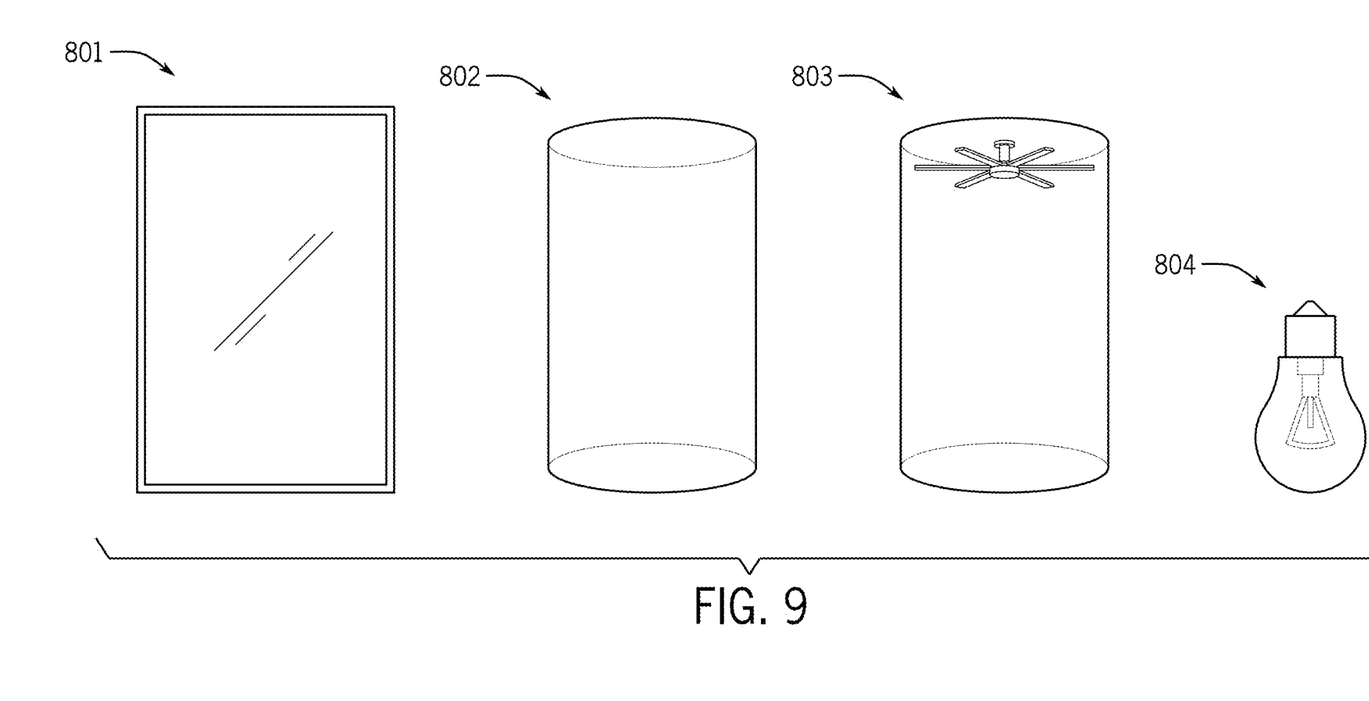
FIG. 9 illustrates example implementations of collector plates.

FIG. 9 illustrates example implementation of the various collection systems including a mirror 801, lighting sconce 802, a light source 803 with fan, and a lamp 804. The lamp 804 is a bulb or other light emitting device that includes a surface coating. Other embodiments may be possible.

The mirror 801 includes a panel for accumulation of aerosol particles in an indoor environment. The reflective surface may be a surface plate. In this example, the electrostatic collector plate may be coupled to the surface plate. Behind the mirror 801 may be an air flow path. The air flow may include aerosol particles. The collector plate is configured to hold an electrical charge to attract and accumulate the aerosol particles.

The lighting sconce 802 may include a panel for accumulation of aerosol particles in an indoor environment. The housing of the sconce 802 may be a surface plate. In this example, the electrostatic collector plate coupled to the surface plate. Air flows through the housing. The collector plate of the sconce 802 is configured to hold an electrical charge to attract and accumulate aerosol particles.

The light source 803 with a fan is another example light fixture with a panel for accumulation of aerosol particles in an indoor environment. Within the light fixture is a plate connected to an electrostatic collector plate. The fan forces are across the electrostatic plate, which is configured to hold an electrical charge to attract and accumulate aerosol particles from the air.

Figure 10:
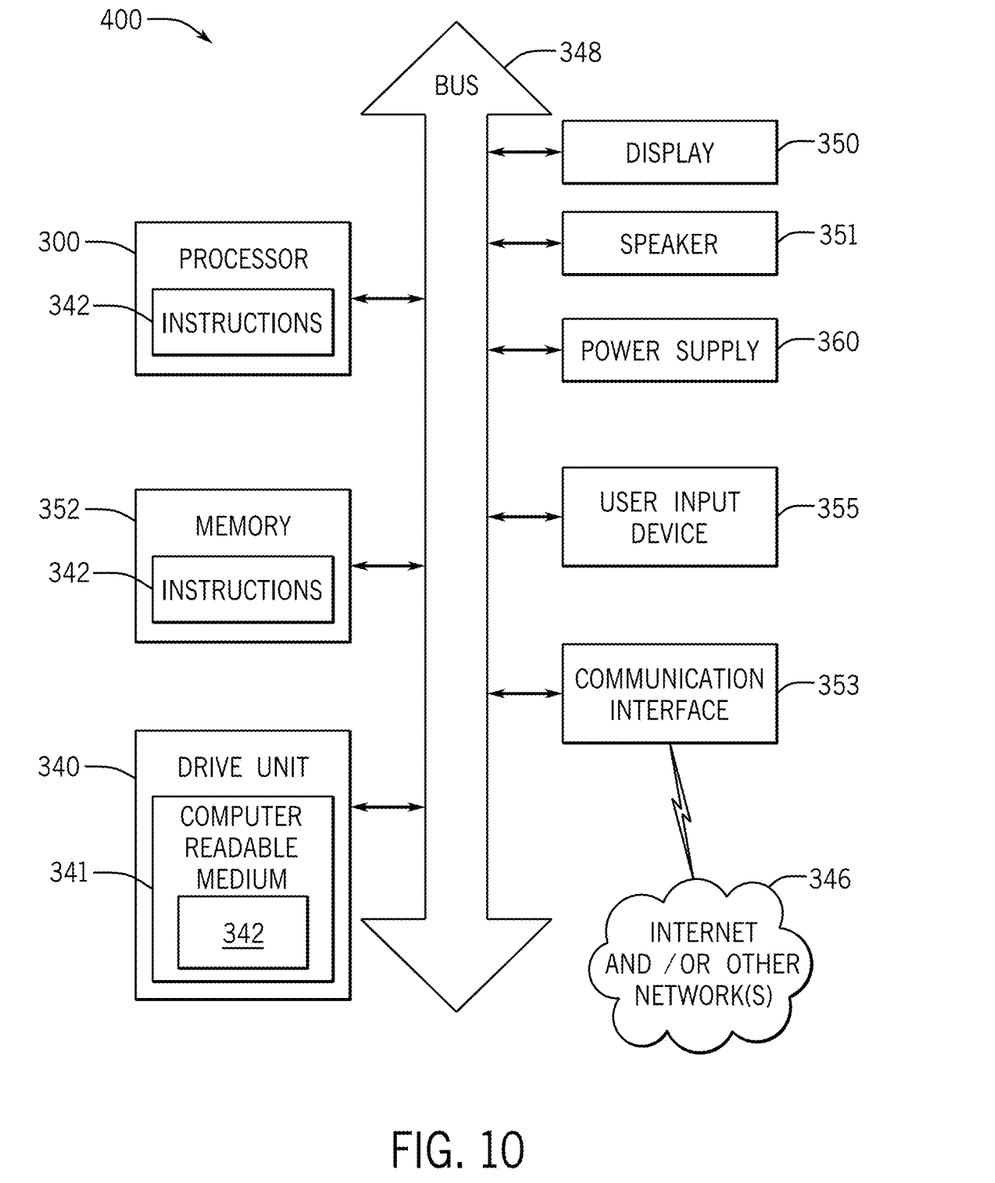
FIG. 10 illustrates a controller.

FIG. 10 illustrates an example controller 400 for the electrostatic charging system. The controller 400 may include a processor 300, a memory 352, and a communication interface 353 for interfacing with devices or to the internet and/or other networks 346. In addition to the communication interface 353. The components of the control system 400 may communicate using bus 348.

Optionally, the control system 400 may include an input device 355 and/or a sensing circuit. The input device 355 may include, a touchscreen coupled to or integrated with the mirror, a keyboard, a microphone for voice inputs, a camera for gesture inputs, and/or another mechanism.

Optionally, the control system 400 may include a drive unit 340 for receiving and reading non-transitory computer media 341 having instructions 342. Additional, different, or fewer components may be included. The processor 300 is configured to perform instructions 342 stored in memory 352 for executing the algorithms described herein. A display 350 may be supported by the mirror frame. The display 350 may be combined with the user input device 355.

Figure 11:
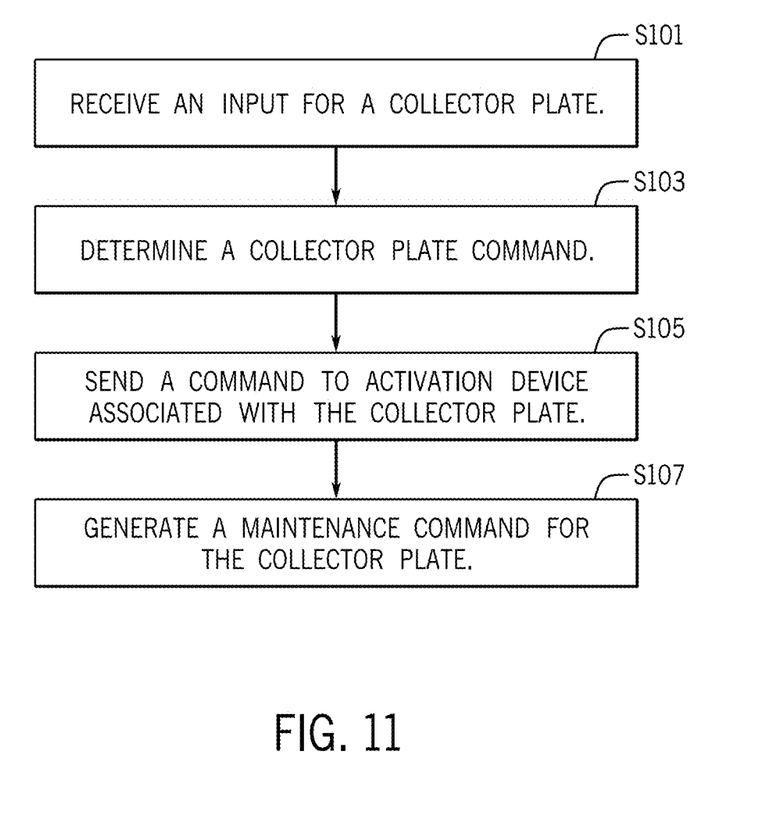
FIG. 11 illustrates a flow chart for the controller of FIG. 10.

FIG. 11 illustrates a flow chart for the control system 400 for the operation of the collection system. The acts of the flow chart may be performed by any combination of the control system 400, the network device or the server. Portions of one or more acts may be performed by the appliance. Additional, different of fewer acts may be included.

At act S101, the controller 400 (e.g., through processor 300) receives an input. The input data may be based on information collected by a sensor. The sensor may determine the presence of particles in a room or other space. The sensor may determine the presence of humans in the room. The sensor may detect the operation of a bathroom appliance, for example, flushing a toilet, turning on or off a faucet, or turning on or off an air dryer. The input may be a user input (e.g., through user input 355) to turn on the collection plate. The input may be setting for the collection plate (e.g., low versus high) or a percentage of aerosols that should be eliminated.

At act S103, the controller 400 (e.g., through processor 300) determines a collector plate command. The collector plate command may turn on power, or set an appropriate power level setting, for the heater, electrostatic charger, fan, light, or other device described herein.

At act S105, the controller 400 (e.g., through processor 300) sends the command to the collector plate. In one example, the command turns the power supply 360 on or off or sets the power level. Thus the command turns on the electrostatic plate, the heater, the fan, the light or other devices described herein.

At act S107, the controller 400 (e.g., through processor 300) sends a maintenance message to the display 350 or the speaker 351. The maintenance message may be provided after a predetermined time has elapsed or based on sensor data related to the number of aerosols in the room or the number of users in the room.

Processor 300 may be a general purpose or specific purpose processor, an application specific integrated circuit (ASIC), one or more programmable logic controllers (PLCs), one or more field programmable gate arrays (FP-GAs), a group of processing components, or other suitable processing components. Processor 300 is configured to execute computer code or instructions stored in memory 352 or received from other computer readable media (e.g., embedded flash memory, local hard disk storage, local ROM, network storage, a remote server, etc.). The processor 300 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions.

The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory.

Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

What is claimed is:

1. A panel for accumulation of aerosol particles in an indoor environment including a toilet, the panel comprising:
    a surface plate;
    an electrostatic collector plate coupled to the surface plate and configured to hold an electrical charge to attract and accumulate aerosol particles; and
    a controller configured to cause the electrostatic collector plate to hold the electrical charge in response to sensor data for the toilet that indicates no user is present at the toilet.

2. The panel of claim 1, further comprising:
    a heating element spaced apart from the electrostatic collector plate by a predetermined distance.

3. The panel of claim 1, further comprising:
    a coating having a disinfectant property, the coating associated with at least a portion of the electrostatic collector plate.

4. The panel of claim 1, further comprising:
    an ultraviolet light source configured to produce an output light with an antimicrobial property, the output light associated with the electrostatic collector plate.

5. The panel of claim 1, wherein the surface plate includes a mirror.

6. The panel of claim 1, further comprising:
    a charging element configured to provide the electrical charge to the electrostatic collector plate.

7. A light fixture comprising:
    a panel for accumulation of aerosol particles in a bathroom including a toilet, the panel comprising:
        a surface plate; and
        an electrostatic collector plate coupled to the surface plate and configured to hold an electrical charge to attract and accumulate aerosol particles;
    a light source to provide light for the light fixture and configured to cause convection to move air including the aerosol particles with respect to the electrostatic collector plate; and
    a controller configured to cause the electrostatic collector plate to hold the electrical charge, wherein the controller is configured to generate a charge command based on sensor data that indicates no user is present at the toilet.

8. The light fixture of claim 7, further comprising:
    a mister configured to generate a mist in the light fixture.

9. The light fixture of claim 8, further comprising:
    a supply for a source liquid for the mister.

10. The light fixture of claim 9, wherein the source liquid includes water or hydrogen peroxide.

11. The light fixture of claim 7, further comprising:
    an ultraviolet light source configured to produce an output light with an antimicrobial property, the output light associated with the electrostatic collector plate.

12. The light fixture of claim 7, further comprising:
    an exterior light configured to illuminate surroundings of the light fixture.

13. The light fixture of claim 7, wherein the sensor data is collected by a motion sensor.

14. A toilet comprising:
    a tank;
    a panel coupled to the tank of the toilet, the panel for accumulation of aerosol particles expelled from a toilet, the panel comprising:

a surface plate; and an electrostatic collector plate coupled to the surface plate and configured to hold an electrical charge to attract and accumulate aerosol particles;

a misting device configured to generate a spray to increase the reactivity of the aerosol particles from the toilet; and a controller configured to cause the electrostatic collector plate to hold the electrical charge, wherein the controller is configured to generate a charge command based on sensor data that indicates no user is present at the toilet.

15. The toilet of claim 14, further comprising:

an ultraviolet light source configured to produce an output light with an antimicrobial property, the output light associated with the electrostatic collector plate.

16. The toilet of claim 14, wherein the misting device includes a piezoelectric element.

\* \* \* \* \*